United States Patent
Davey et al.

(10) Patent No.: US 7,183,326 B2
(45) Date of Patent: Feb. 27, 2007

(54) INSTALLATION AND METHOD FOR PRODUCING AND DISAGGREGATING SYNTHESIS GASES FROM NATURAL GAS

(75) Inventors: William Davey, Frankfurt am Main (DE); Manfred Meyer, Friedrichsdorf (DE); Jürgen Hofmockel, Frankfurt am Main (DE)

(73) Assignee: Lurgi AG, Frankfurt am Main (DE)

( * ) Notice: Subject to any disclaimer, the term of this patent is extended or adjusted under 35 U.S.C. 154(b) by 243 days.

(21) Appl. No.: 10/503,485

(22) PCT Filed: Mar. 22, 2003

(86) PCT No.: PCT/EP03/03011

§ 371 (c)(1),
(2), (4) Date: Aug. 3, 2004

(87) PCT Pub. No.: WO03/106393

PCT Pub. Date: Dec. 24, 2003

(65) Prior Publication Data

US 2005/0107480 A1    May 19, 2005

(30) Foreign Application Priority Data

Jun. 13, 2002    (DE) ............................... 102 26 209

(51) Int. Cl.
C07C 27/00    (2006.01)
C01C 1/04    (2006.01)

(52) U.S. Cl. ...................... 518/700; 518/702; 518/703; 518/704; 423/359

(58) Field of Classification Search ................ 518/700, 518/702, 703, 704; 423/359
See application file for complete search history.

(56) References Cited

U.S. PATENT DOCUMENTS 4,315,900 A * 2/1982 Nozawa et al. .............. 423/359
4,886,651 A * 12/1989 Patel et al. .................. 423/359

* cited by examiner

*Primary Examiner*—J. Parsa
(74) *Attorney, Agent, or Firm*—Andrew Wilford; Jonathan Myers

(57) ABSTRACT

What is described is a method and an installation for the simultaneous production of methanol synthesis gas, ammonia synthesis gas, carbon monoxide and carbon dioxide from natural gas, in which several plant elements (or plant units) are serially arranged one by one in one single production chain, whereat these elements comprise:

Figure 1:
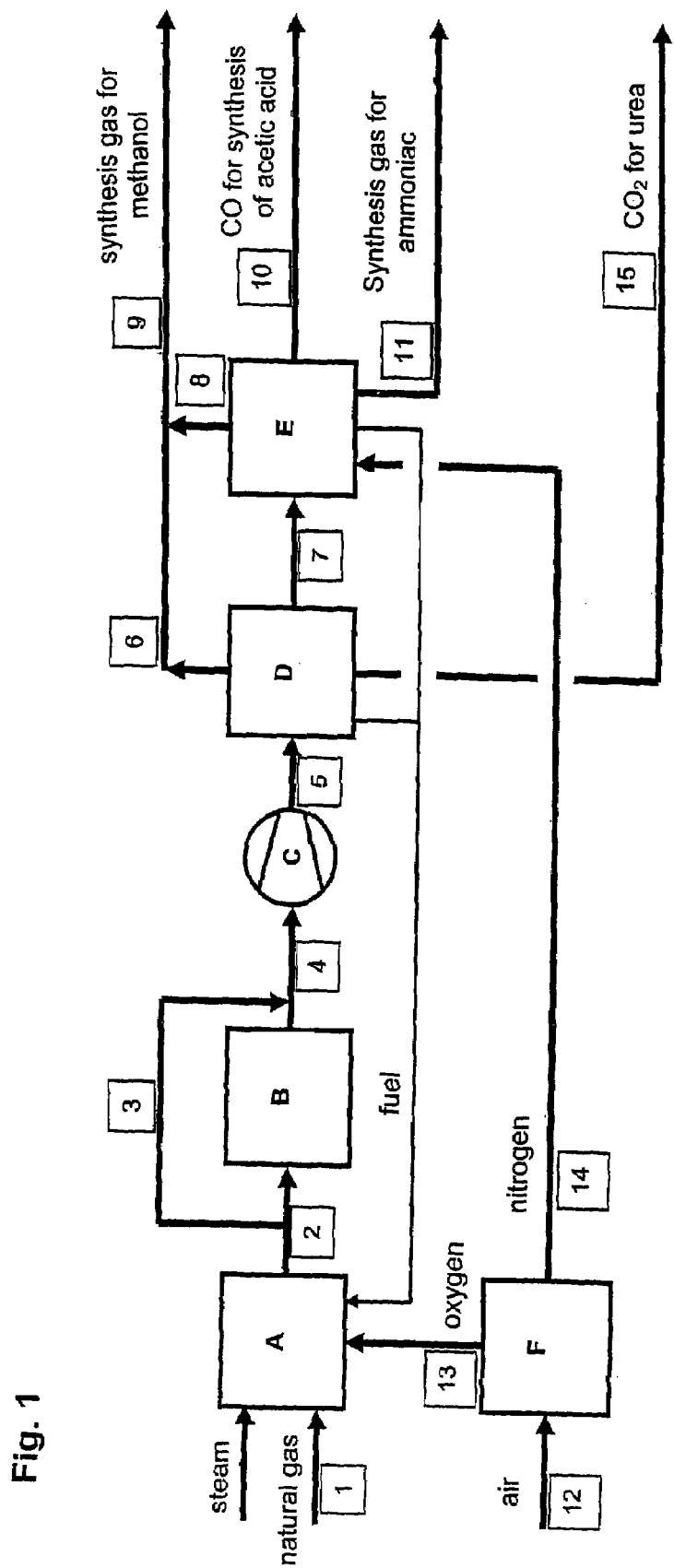

a first reactor A, in which the natural gas is transformed under oxygen supply into a synthesis gas mixture comprised of carbon monoxide, carbon dioxide, hydrogen and steam (water vapor), a second reactor B, which allows to control the transformation of carbon monoxide into carbon dioxide, optionally a compressor C for compressing the generated gases, an absorber D for the absorption of carbon dioxide and for obtaining the carbon monoxide-hydrogen mixture used for methanol synthesis, a low-temperature separator E, in which ammonia synthesis gas is obtained by introducing liquid nitrogen, and in which simultaneously carbon monoxide, argon and methane are removed.

8 Claims, 1 Drawing Sheet

INSTALLATION AND METHOD FOR PRODUCING AND DISAGGREGATING SYNTHESIS GASES FROM NATURAL GAS

Subject of the invention is a plant and a method for the simultaneous production of synthesis gases like methanol synthesis gas, ammonia synthesis gas, carbon monoxide and carbon dioxide by fractionating a gas mixture generated from natural gas.

For the production of methanol, ammonia, pure carbon monoxide, carbon dioxide and other synthesis gases it is known to erect production plants, in each of which in general only one of the afore mentioned gases can be produced [(2) and (3)]. Only methods for the simultaneous production of methanol and ammonia are already known from the German published patent application DE 33 36 649, the Japanese patent application JP 200 006 3115 and from the European patent 0 853 608. A technically important approach suitable for this aim comprises the transformation of a naturally occurring natural gas into a synthesis gas containing carbon monoxide, carbon dioxide and hydrogen as major components. Methods for the production of synthesis gas have been described e.g. in the German published patent application DE 33 45 064 and in the European patent application EP-A 0 999 178.

For economical reasons however, it would be extremely advantageous if it was possible to perform a such complete fractionation of the components of a synthesis gas in one single production plant, that methanol synthesis gas, ammonia synthesis gas, carbon monoxide and carbon dioxide could be obtained in one single production chain in a highly pure form to be directly available for further chemical syntheses. Such a combined gas fractionation plant would be particularly efficient not only for reason of the obtainable savings in consequence of increased production outputs, but also because several elements of the production plant—in contrast to a higher number of separate plants each of which is adapted to just one single product—would be required only as a single specimen. A plant of this kind could be particularly economical if it was possible to realise it in such a flexible manner, that one is allowed to adapt the amounts of the different gases obtained from that plant to the actual needs.

It has now be been discovered, that these requirements can be fulfilled by a plant for the simultaneous production of methanol synthesis gas, ammonia synthesis gas, carbon monoxide and carbon dioxide from natural gas, if the following plant elements (or plant units) are serially arranged one by one in one single production chain:

- a first reactor A, in which the natural gas is transformed under oxygen supply into a synthesis gas mixture comprised of carbon monoxide, carbon dioxide, hydrogen and water,
- a second reactor B, which allows to control the transformation of carbon monoxide into carbon dioxide,
- optionally a compressor C for compressing the generated gases,
- an absorber D for the absorption of carbon dioxide and for obtaining the carbon monoxide-hydrogen mixture used for methanol synthesis,
- a low-temperature separator E, in which ammonia synthesis gas is obtained by introducing liquid nitrogen, and in which simultaneously carbon monoxide, argon and methane are removed.

BRIEF DESCRIPTIONS OF DRAWING

The reaction process is schematically depicted in the enclosed FIG. 1.

The first reactor A serves to produce synthesis gas and allows for the desulphurization of the employed gas mixture, its saturation with steam (water vapour), the heating in a heater under catalytic degradation of higher hydrocarbons (longer chain hydrocarbons) into methane, the partial oxidation with oxygen, and a cooling of the gas under the production of steam. Such a plant element, also designated as a CPox reactor (catalytic partial oxidation), is frequently employed in the construction of plants and is described in literature (1). It constitutes a cylindrical vessel having vertically arranged, arcuate walls. A burner or a mixer is provided in the upper part of the vessel, into which a naturally occurring natural gas mixed with steam, steam itself and oxygen are each introduced via separate feeding lines. The burner or mixer supports a thorough mixing of these three gas streams in the upper part of the vessel, in which the major portion of the partial oxidation is accomplished very quickly. The hot gases are then passed over a catalyst present in the bottom part of the vessel, where the transformation of the natural gas is completed. The catalytic partial oxidation can be characterised by the following chemical reaction equations:

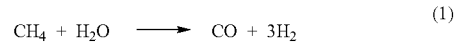  (1)
  (2)
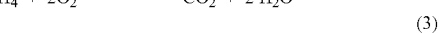  (3)
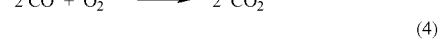  (4)
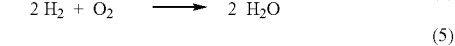  (5)

Steam is fed to the reactor A in such an amount, that one reaches a molar ratio of steam to non-oxidised hydrocarbons of 1.4 up to 3.0, preferably of 1.7. Oxygen is fed to the reactor A in an amount, that the molar ratio of oxygen to non-oxidised hydrocarbons is 0.45 up to 0.7, preferably 0.52. The exact amount of oxygen in practice is thereby controlled, that the starting temperature of the gas mixture from reactor A is adjusted to temperatures between 900 and 1050° C., in general to 950° C. The purity of the oxygen supplied by the air separation plant F (see FIG. 1) in general ranges between 90 and 99.5%, but usually is about 99.5%. The catalyst used in the reactor A is a nickel oxide catalyst, e.g. a catalyst of the types G-31E, G-90LDP or G-90B, which can be obtained from the Sud-Chemie AG, Munich, Germany. The transformation of the natural gas into a synthesis gas is accomplished at a pressure of 20 to 100 bar, preferably at a pressure of about 40 bar. The reactor A is connected to a second reactor B, in which the generation of carbon dioxide from carbon monoxide can be controlled while simultaneously producing hydrogen. The reactor B however also provides a bypass [3], via which the synthesis gas mixture produced in the first reactor A can be entirely or partially guided past the reactor B, thus allowing to control the degree of transformation of the gas mixture. In the reactor B, the oxidation of carbon monoxide to carbon dioxide is accomplished as a one- or two-step process with intermediate cooling in the presence of high temperature catalysts.

If there is no need or only a little need for carbon dioxide, the synthesis gas obtained from reactor A is guided past the reactor B and is then, via line [4], immediately fed into a compressor C, which allows to compress the generated gas mixture. Compressor C serves to compress the gas generated in reactor A to a pressure between 60 and 100 bar, in general to a pressure of 80 bar. However, if the pressure of the gas withdrawn from reactor A is already over 40 bar, the use of a compressor can be omitted. The compressor employed in this context is a well known device as it is commonly used in many chemical plants.

Starting from the compressor C, the gas mixture is then fed to the absorber D via line [5], whereat the absorber serves to remove the carbon dioxide from the gas mixture. This may either be accomplished in a physical or chemical way. In a physical gas cleaning, the carbon dioxide is absorbed by cold methanol or by cold glycol ether. In a chemical washing, the absorption is preferably accomplished by an alkanol amine, sodium carbonate or another alkaline substance. Preferably, the absorber D provides two reaction steps, whereat in the first reaction step a rough separation of the carbon dioxide is accomplished, leading to a molar concentration between 1–10% by weight, calculated on the basis of the dry gas, preferably however it is a removal of up to a concentration of 2.2% by weight. In the second absorption step, the remaining carbon dioxide is then removed, thereby reaching a molar concentration of less than 50 ppm, preferably of less than 10 ppm. The absorber D also comprises a means for a controlled reduction of the gas pressure of the absorbent in order to thereby allow for a recovery of carbon dioxide. The absorber D moreover comprises means for regenerating the absorbent by applying heat, means for maintaining a constant composition of the absorbent and also for adjusting the solvent's gas pressure to the process pressure. The carbon dioxide recovered that way can be entirely or partially used for subsequent syntheses, e.g. for the production of urea. Excess carbon dioxide is discharged to the atmosphere. Several other methods for removing the carbon dioxide are described in the references (2), (3) and (4).

The gas mixture, now being free from carbon dioxide, is then fed via line [7] to the low temperature separator E, in which a partial condensation and separation of carbon monoxide and hydrogen is accomplished by introducing liquid nitrogen. This method is described in detail in the German patent application 102 26 210.1, which has been filed at the same date. In consequence, a methanol synthesis gas being comprised of carbon monoxide and hydrogen, is obtained. The purity of the carbon monoxide obtained from the low temperature separator E can be further improved by a methane purification.

The carbon monoxide obtained in the low temperature separator E can also be fed to a plant for the production of acetic acid by a carbonylation of methanol.

Contaminations with methane or argon are as well removed by the nitrogen washing in the low temperature separator E; these contaminations may then be used as a fuel gas for the heat production in reactor A.

In the low temperature separator E, the gas is cooled off to a temperature in the range between −200° C. and −150° C. At this temperature, the gas is subjected to a flash evaporation in one or more evaporator drums, thereby separating hydrogen from carbon monoxide. At first, the flash evaporations yield a liquid hydrogen, which is rich in carbon monoxide. The gaseous carbon monoxide gas is washed with liquid carbon monoxide in order to purify the gas and to remove methane, after which the carbon monoxide gas is reheated to room temperature. The hydrogen is then passed through a second washing column, where it is washed with liquid nitrogen in order to remove traces of carbon monoxide, argon and methane. The molar ratio of hydrogen to nitrogen is then adapted to a value of 3:1 in order to obtain a gas mixture being suitable for ammonia synthesis.

The low temperature separator E moreover comprises a molecular sieve in order to remove traces of carbon dioxide already before the low temperature separation takes place, thus yielding a carbon dioxide-free synthesis gas. The low temperature separator E as well is a known plant element and is described in detail in reference (5).

The plant element F being depicted in FIG. 1 is a common air separation plant producing a stream of oxygen with a purity between 90 and 99.5%. The plant element F moreover provides nitrogen with a purity of over 99.995%.

The gases obtained in the plant according to the invention and according to the afore mentioned methods are produced in a such highly pure form, that they can be used for subsequent chemical syntheses.

The efficiency of the plant according to the invention, here being adapted to the production outputs given in the following, and the method for the fractionation of a synthesis gas to be accomplished therein, is illustrated by the following example:

a) It is intended to produce 4000 tons of methanol per day, a part of which is employed for the production of acetic acid. The synthesis of methanol requires a composition of the synthesis gas with a stoichiometric number $S_n$ of 2.05, a carbon dioxide concentration in the range between 2 and 3% and a nitrogen concentration of less than 0.5%. The stoichiometric number ($S_n$) is calculated according to the following formula:

$$S_n = \frac{([H_2] - [CO_2])}{([CO_2] + [CO])}$$

In this formula, $[H_2]$ $[CO_2]$ and $[CO_2]$ $[CO]$ represent the molar concentrations of hydrogen, carbon dioxide and carbon monoxide in the synthesis gas;

b) Simultaneously, one can yield synthesis gases for 1200 tons of acetic acid per day from the same plant. The production of acetic acid requires methanol and carbon monoxide with a purity of at least 98%;

c) Furthermore, synthesis gases for 4000 tons of ammonia per day can be obtained from the same plant, a part of which is used is used for the production of urea. The production of ammonia requires a mixture of hydrogen and nitrogen in a molar ratio of 3:1, whereat the gas mixture must contain less than 10 ppm of oxygen.

d) Finally one can moreover obtain synthesis gases for 6270 tons of urea per day from the same plant. The production of urea requires pure ammonia as well as carbon dioxide with a purity of more than 98.5%.

These requirements can be fulfilled by using the following procedure, whereat the composition of the individual gas streams is given in table 1:

1. The raw synthesis gas produced from natural gas is generated in the reactor A and adjusted to a pressure of about 45 bar. It leaves reactor A with the composition [2];
2. About 82% of the raw synthesis gases from reactor A are guided past the reactor B as a gas stream [3], whereas 18% of the raw synthesis gas are subjected to a controlled transformation of carbon monoxide into carbon dioxide accomplished in reactor B. The gas stream leaving the reactor B is then united with the gas stream [3] in order to form a gas stream [4];

3. The cooled and condensed gas stream [4] is then compressed to a pressure of about 80 bar in the compressor C;
4. The compressed gas is fed to the absorber D, from which about 43% of the synthesis gas is withdrawn, when the carbon dioxide absorbent reaches a mean degree of saturation and when the carbon dioxide concentration is reduced to about 2.2%. The gas then has the composition of the gas stream [6]. The remaining gas is subjected to a second absorption during a carbon dioxide intensive purification, whereat at carbon dioxide concentration of less than 10 ppm is achieved. This gas is fed as a gas stream [7] into the low temperature separator E.
5. In the low temperature separator E, carbon monoxide is separated from the synthesis gas, whereat the carbon monoxide is then utilized as a gas stream [10] for acetic acid synthesis or as gas stream [11] for ammonia synthesis or as a stream of residual gas (gas stream [8]), whereat the gas stream 8 is united with the methanol synthesis gas in a gas stream [9]. Contaminations of the synthesis gas like methane, argon and carbon monoxide are employed as a fuel gas and fed to the burner of reactor A;
6. The carbon dioxide obtained from the absorber D is employed for urea synthesis via the substance stream [15].

The above described fractionation of the synthesis gas into several individual fractions in one single plant is just one example for the nearly unlimited potential of supplying gas mixtures required for specific chemical syntheses by means of combining the plant elements contained in the plant according to the invention with chemical transformation methods. By means of suitable modifications and alterations of the individual plant elements and process steps it is as well possible to obtain also specific gas mixtures from natural gas in one single plant, whereat these gas mixtures may be then e.g. be employed for other important syntheses like the Fischer-Tropsch synthesis, the oxo-alcohol synthesis, the ethylene glycol synthesis and other processes.

REFERENCES

1. Hermann Göhna, "Concepts for Modern Methanol Plants". Proceedings of the 1997 World Methanol Conference, Tampa, Fla., USA (December 1997)
2. "Gas Production", Ulimans's Encyclopedia of Industrial Chemistry, Vol. A12, VCH Verlagsgesellschaft mbh (1989)
3. Max App "Ammonia, Methanol, Hydrogen, Carbon Monoxide, Modern Production Technologies". British Sulphur Publishing—a Division of CRU Publishing Ltd., 31 Mount Pleasant, London WC1X 0AD. ISBN 1 873387 26 1 (published 1997)
4. Emil Supp "How to produce Methanol from Coal". Springer-Verlag (1990)
5. W L E Davey "Cold Box for the Production of Multiple Products from a Stream of Syngas". German Patent Application No. ? (2002) (L1P13)

TABLE I

| | Gas stream | | | | | | | | | | | | | | |
|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 |
| Composition (% by volume) | | | | | | | | | | | | | | | |
| Methane | 95.4 | 1.64 | 1.64 | 2.39 | 2.39 | 2.41 | 2.47 | 5.67 | 2.89 | 0.57 | | | | | 0.60 |
| Ethane | 3.91 | | | | | | | | | | | | | | |
| Propane | 0.03 | | | | | | | | | | | | | | |
| Carbon monoxide | | 13.88 | 13.88 | 17.71 | 17.72 | 19.32 | 19.73 | 85.41 | 29.96 | 98.19 | <5 ppm | | | | 0.4 |
| Carbon dioxide | 0.59 | 6.65 | 6.65 | 12.18 | 12.19 | 2.24 | | | 1.91 | | | | | | 98.5 |
| Argon | | 0.06 | 0.06 | 0.08 | 0.08 | 0.09 | 0.09 | 0.40 | 0.14 | 0.36 | <150 ppm | 0.40 | 0.50 | 0.01 | |
| Hydrogen | | 44.56 | 44.56 | 67.42 | 67.47 | 75.95 | 77.71 | 8.52 | 65.97 | 0.87 | 75.00 | | | | 0.5 |
| Nitrogen | 0.08 | 0.02 | 0.02 | 0.02 | 0.02 | | | | | | 25.00 | 79.0 | | 99.99 | |
| Oxygen | | | | | | | | | | | | 20.6 | 99.5 | | |
| Water | | 33.18 | 33.18 | 0.19 | 0.11 | | | | | | | | | | |
| Temp. (° C.) | 22 | 412 | 412 | 40 | 41 | 36 | 36 | 36 | 36 | 36 | 36 | 22 | 36 | 36 | 32 |
| Pressure (bar abs) | 23 | 39.6 | 39.6 | 37.2 | 79.3 | 77.8 | 76.3 | 76.3 | 5 | 76.3 | 1.0 | 45 | 55.0 | 1.2 | |
| Rate of flow (t/h) | 207 | 820 | 668 | 483 | 482 | 121 | 147 | 63 | 185 | 24 | 168 | 1.058 | 208 | 154 | 192 |

The invention claimed is:

1. A method for the simultaneous production of methanol synthesis gas, ammonia synthesis gas, carbon monoxide and carbon dioxide from natural gas which comprises the steps of (a) introducing steam, oxygen, and natural gas into an installation for the simultaneous production of methanol synthesis gas, ammonia synthesis gas, carbon monoxide and carbon dioxide, which comprises in a serial arrangement, one by one, in one single production chain:

a first reactor A, in which the natural gas is transformed under oxygen supply into a synthesis gas mixture comprised of carbon monoxide, carbon dioxide, hydrogen and steam;

a second reactor B, which controls transformation of carbon monoxide into carbon dioxide, an absorber D for absorption of the carbon dioxide and for obtaining a carbon monoxide—hydrogen mixture used for methanol synthesis; and a low-temperature separator E, in which ammonia synthesis gas is obtained by introducing liquid nitrogen, and in which simultaneously carbon monoxide, argon and methane are removed;

wherein in the first reactor the molar ratio of steam to non-oxidized hydrocarbons is 1.5 up to 3.0;

(b) transforming the natural gas into a synthesis gas;

(c) compressing the synthesis gas to a pressure of 60 to 100 bar;

(d) absorbing carbon dioxide from the compressed synthesis gas to obtain as products a synthesis gas with a reduced carbon dioxide content and carbon dioxide;

(e) dividing the synthesis gas with a reduced carbon dioxide content into two portions and using the first portion as a methanol synthesis gas containing hydrogen, carbon monoxide, and carbon dioxide and subjecting the remaining portion to a second more intensive carbon dioxide absorption to obtain a synthesis gas having a carbon dioxide content of less than 10 ppm; and (f) introducing the synthesis gas having a carbon dioxide content of less than 10 ppm and liquid nitrogen into a low temperature separator to obtain as products an ammonia synthesis gas comprising hydrogen and nitrogen, and carbon monoxide, which may be united with the methanol synthesis gas, and separating the ammonia synthesis gas from the carbon monoxide, wherein steps (a) through (f) are carried out, one by one, in a single production chain.

2. Method according to claim 1, wherein according to step (a) in the first reactor the molar ratio of oxygen to non-oxidised hydrocarbons is 0.45 up to 0.7.

3. Method according to claim 1, wherein according to step (b) a catalyst containing nickel oxide is used for transforming the natural gas into a synthesis gas.

4. Method according to claim 1, wherein according to step (b) for transforming the natural gas into a synthesis gas, a pressure of 25 to 100 bar.

5. Method according to claim 1, wherein according to step (b) for the oxidation of carbon monoxide to carbon dioxide in the second reactor B, a one- or two-step method with intermediate cooling in the presence of high temperature catalysts is performed.

6. Method according to claim 1, wherein according to step (c) the synthesis gas produced in the reactors A and B is adjusted by means of the compressor C to a pressure of 80 bar.

7. Method according to claim 1, wherein according to step (d) in the absorber D the carbon dioxide is separated from the synthesis gas in one or more process steps in a chemical or physical way.

8. Method according to claim 1, wherein according to step (f) the synthesis gas is cooled off to temperatures of −150° C. to −200° C. in the separator by introducing liquid nitrogen and that thereby methane, argon and carbon monoxide are removed and that the remaining hydrogen gas is mixed with nitrogen in a molar ratio of 3:1 in order to obtain ammonia synthesis gas.

* * * * *